United States Patent [19]

Morris

[11] Patent Number: 5,380,320

[45] Date of Patent: Jan. 10, 1995

[54] ELECTROSURGICAL INSTRUMENT HAVING A PARYLENE COATING

[75] Inventor: James R. Morris, Sedalia, Colo.

[73] Assignee: Advanced Surgical Materials, Inc., Littleton, Colo.

[21] Appl. No.: 149,059

[22] Filed: Nov. 8, 1993

[51] Int. Cl.⁶ .................................... A61B 17/36
[52] U.S. Cl. .................................... 606/33; 606/32; 606/39; 606/40; 606/45
[58] Field of Search .................................... 606/32–52

[56] References Cited

U.S. PATENT DOCUMENTS

| | | | |
|---|---|---|---|
| 4,142,531 | 3/1979 | Magovern et al. | 607/128 |
| 4,225,647 | 9/1980 | Parent . | |
| 4,326,529 | 4/1982 | Doss et al. | 605/41 |
| 4,662,382 | 5/1987 | Sluetz et al. | 607/126 |
| 4,921,723 | 5/1990 | Nicholas et al. | 427/41 |
| 5,026,370 | 6/1991 | Lottick | 606/42 |
| 5,147,357 | 9/1992 | Rose et al. | 606/49 |
| 5,176,702 | 1/1993 | Bales et al. | 606/205 X |

*Primary Examiner*—Peter A. Aschenbrenner
*Attorney, Agent, or Firm*—Dorr, Carson, Sloan & Peterson

[57] ABSTRACT

An electrosurgical instrument has a conductive elongated member, a connector for connecting an external electrical power supply to the proximal end of the elongated member, an electrosurgical implement at the distal end of the elongated member, and an insulative parylene coating covering the elongated member. The thickness of the parylene coating is in the range of approximately 1 to 6 mil inches, and preferably 2 to 3.5 mil inches. In the preferred embodiment, the surfaces of the instrument that are to remain uncoated are first masked. The unmasked surfaces are roughened and then dipped in a liquid silicone. The parylene coating is then applied by vacuum vapor phase deposition and annealed. A parylene coating can also be applied to portions of the electrosurgical implement for insulation. A thin parylene coating can be applied to the blade of the instrument as a non-stick coating for easier cleaning. If the instrument is an endoscopic electrosurgical instrument used with a trocar sleeve having a valve to receive the shaft, wear between the valve and the shaft can be reduced by applying a parylene coating to the interior surface of the valve.

27 Claims, 5 Drawing Sheets

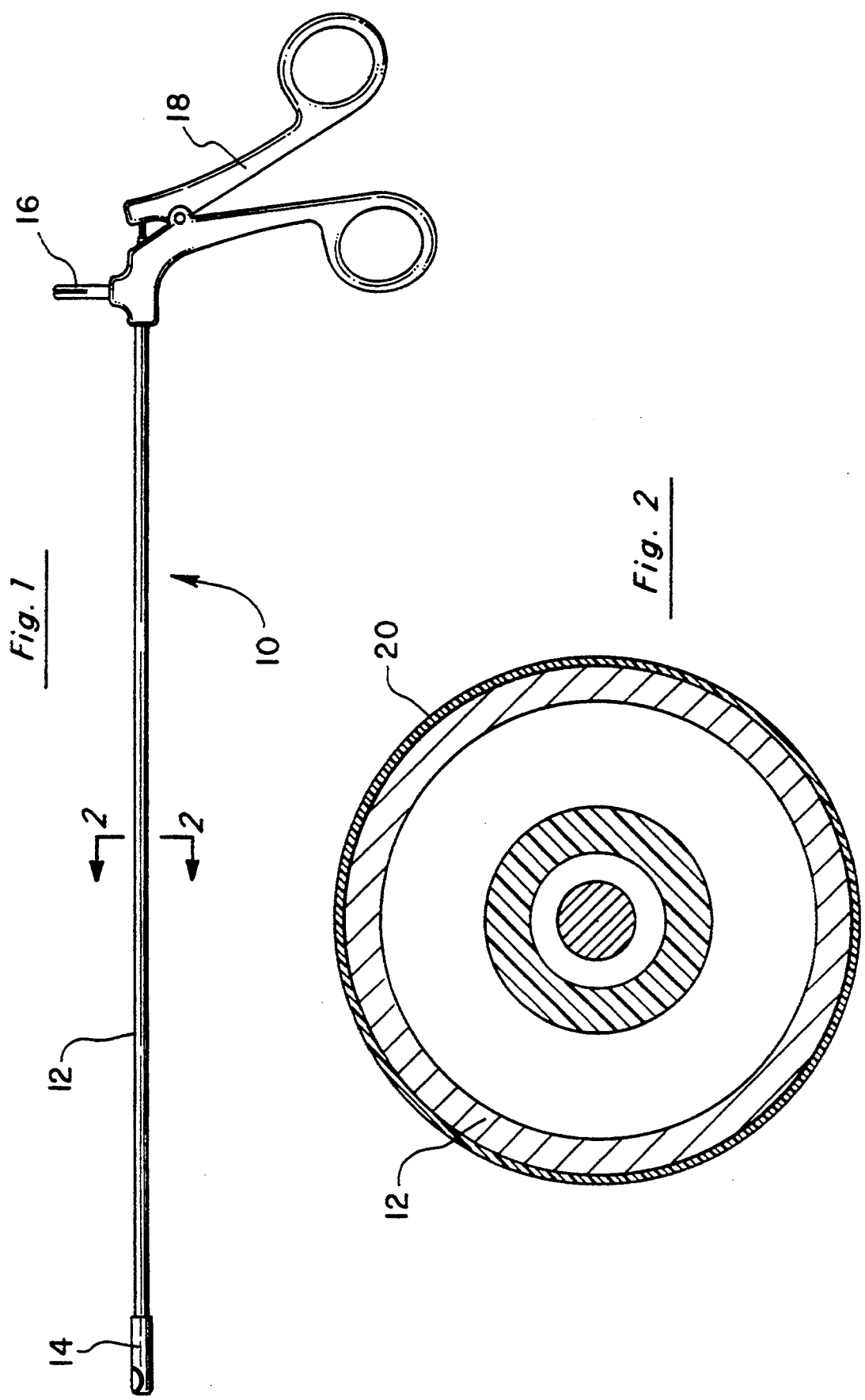

ELECTROSURGICAL INSTRUMENT HAVING A PARYLENE COATING

BACKGROUND OF THE INVENTION

FIELD OF THE INVENTION

The present invention relates generally to the field of electrosurgical instruments. More specifically, the present invention discloses an electrosurgical instrument having an insulative coating of parylene.

STATEMENT OF THE PROBLEM

Electrosurgical instruments are widely used in a variety of shapes and configurations to cut tissue by means of high-voltage, high-frequency electrical energy. A number of examples of electrosurgical instruments are shown in the drawings. In general, an electrosurgical instrument has an elongated conductive member (e.g., a metallic shaft), a connector for connecting an external electrical power supply to the conductive member, and an electrosurgical implement at the distal end of the conductive member. Many electrosurgical instruments also have a grip at the proximal end of the conductive member to facilitate manipulation of the instrument. The conductive member requires an insulative coating to ensure that electrical energy is carried only to the implement at its distal end, rather than being discharged elsewhere along the length of the electrosurgical instrument. Most electrosurgical instruments operate at approximately 3000 to 4000 volts, and sometimes up to 16 kV. Therefore an extremely high degree of care must be taken to protect against breaks or defects in the insulative layer to eliminate the risk of injury to the patient, surgeon, or other medical personnel.

The insulative coating on electrosurgical instruments must also be able to withstand wear and abuse typical for medical instruments used in hospitals. In particular, an insulating material for electrosurgical instruments should have the following characteristics:

A. Complete bio-compatibility to avoid adverse reactions with the patient's tissue.
B. Excellent dielectric strength.
C. A low and constant dissipation factor over a wide range of frequencies (e.g., 60 Hz to 1 MHz).
D. A low and uniform dielectric constant over a wide range of frequencies.
E. Good wear and adhesion properties.
F. Ability to withstand high operating temperatures and autoclave sterilization temperatures.
G. Excellent chemical/moisture barrier properties.
H. Excellent resistance to degradation from gamma radiation used for sterilization.
I. Ability to be economically applied to a large number of instruments.
J. Ability to selectively insulate edges, corners, ends, and inner diameters of instruments.

Polyethylene heat-shrink tubing has typically been used as the means for providing electrical insulation on monopolar and bipolar electrosurgical instruments. While polyethylene tubing is an excellent electrical insulator, it suffers from several disadvantages when used in electrosurgical instrumentation. First, heat-shrink tubing does not bond directly to the instrument. This leads to sterility problems because blood and body fluids can become trapped in the area between the tubing and the instrument. This is especially true in endoscopic surgical applications when the patient is insufflated. The elevated air pressure within the patient's body tends to force blood and body fluids into the space between the heat-shrink tubing and the instrument.

Second, heat-shrink tubing cannot be readily used to insulate edges, ends, inner diameters, or corners of surgical instrumentation. Third, the heat-shrink tubing must be applied individually to each surgical instrument, thereby increasing labor costs. Finally, polyethylene tubing has a relatively low operating temperature range. Polyethylene tubing becomes soft and its resistance to cutting is lowered when heated through steam autoclave sterilization procedures commonly used in most hospitals. This substantially increases the tubing's susceptibility to failure. Heat-shrink tubing can also become soft during normal operation of electrosurgical instruments as a result of the high current densities used in electrosurgical instruments and the heating that inherently occurs at the working end of such instrumentation.

In addition to polyethylene heat-shrink tubing, other less common forms of electrical insulative protection for electrosurgical instruments are epoxides, urethanes, ceramic composites, and silicones. For example, U.S. Pat. No. 4,785,807 of Blanch, issued on Nov. 22, 1988, discloses an electrosurgical knife having a non-stick coating made of a fluorinated hydrocarbon material, such as Teflon. These materials usually lack several of the desirable characteristics outlined above (i.e., ability to selectively insulate specific areas of instrumentation, bio-compatibility, economics, dielectric constant, etc.). With the exception of ceramic composites, most of these materials must be applied to the instrument through a dip process. This method of application does not lend itself to selective insulation of desired areas on the instrument. Each instrument must be manipulated individually, thereby reducing economies of scale in production. Voids or bubbles can be formed that often result in defects in the insulation. Ceramic composites are generally brittle and can suffer insulation failure if the instrument is flexed or bent. In addition, ceramic composites must be applied individually to each instrument, which greatly increases production costs, and ceramic composites are difficult to apply only to selected areas of the instrument.

Parylene is the generic name for thermoplastic film polymers based on para-xylylene and made by vapor phase polymerization. Parylene N coatings are produced by vaporizing a di(p-xylylene) dimer, pyrolyzing the vapor to produce p-xylylene free radicals, and condensing a polymer from the vapor onto a substrate that is maintained at a relatively low temperature, typically ambient or below ambient. Parylene C is derived from di(monochloro-p-xylylene) and parylene D is derived from di(dichloro-p-xylylene). Parylenes have previously been recognized as having generally good insulative, chemical resistance and moisture barrier properties. However, conventional parylene films do not generally adhere well to many substrate surfaces, particularly under wet conditions. Although these polymers are quite resistant to liquid water under most conditions, conventional parylene films are subject to penetration by water vapor, which can condense at the interface between the parylene film and the substrate, forming liquid water, which tends to delaminate the film from the substrate. In addition, conventional parylene films formed by vapor deposition are generally quite crystalline and are subject to cracking or flaking, which can expose the substrate below the film.

Parylene coatings have been used in the past in a wide variety of other fields, including the following:

| Inventor | Patent No. | Issue Date |
| --- | --- | --- |
| Christian et al. | 5,174,295 | Dec. 29, 1992 |
| Frachet et al. | 5,144,952 | Sept. 8, 1992 |
| Taylor et al. | 5,067,491 | Nov. 26, 1991 |
| Evans | 4,950,365 | Aug. 21, 1990 |
| Nichols et al. | 4,921,723 | May 1, 1990 |
| Bongianni | 4,816,618 | Mar. 28, 1989 |
| Bongianni | 4,581,291 | April 8, 1986 |
| Japanese Patent 1297093 | | Nov. 30, 1989 |

Christian et al. disclose a system for measuring blood flow using a Doppler crystal 251 having a thin protective coating of parylene (col. 19, line 57–col. 20, line 2).

Frachet et al. disclose a transcutaneous electrical connection device placed through the pinna of the ear or through the earlobe. The device includes at least one subcutaneous wire covered with an insulating sheath that is fixed to a metal ball positioned on the surface of the ear and covered with an insulating material on the part of its outer surface in contact with the ear. The insulating material and sheath are made of a bio-compatible material such as Teflon or parylene.

Taylor et al. disclose a blood pressure-monitoring device for insertion into a patient's blood stream. The blood pressure-sensing element and catheter are conformably coated with a thin layer of parylene to insulate the device from the deleterious effects that blood components such as water and ions would otherwise have on various components of the device.

Evans discloses a process for coating a metal substrate by first applying a thin hard coated layer of titanium nitride, titanium carbide, or the like, and then a second coat of parylene.

Nichols et al. disclose a process for applying an adherent electrically insulative moisture-resistant composite insulative coating to a substrate by glow discharge polymerization. Various parylenes are discussed as possible coating materials.

The Bongianni patents disclose a microminiature coaxial cable having a very thin ribbon strip conductor surrounded by a foamed dielectric or parylene. A thin coating of parylene is also applied to the outer conductor to prevent oxidation and inhibit mechanical abrasion.

Japanese Patent 1297093 discloses a pill cutter for woolen clothes in which a thin film of parylene (poly-para-xylylene) is formed on the surface of the cutting blade.

SOLUTION TO THE PROBLEM

None of the prior art references uncovered in the search show an electrosurgical instrument having an insulative coating made of annealed parylene. This coating provides complete bio-compatibility, excellent dielectric strength, a low and constant dissipation factor and dielectric constant over a wide range of frequencies, good wear and adherence properties on metallic surgical instruments, the ability to withstand high operating temperatures, and excellent chemical and moisture barrier properties. In addition, a parylene coating can be applied to a large number of instruments very economically by vacuum vapor phase deposition. A parylene coating can also be used to selectively insulate edges, corners, ends, and inner diameters of electrosurgical instruments.

SUMMARY OF THE INVENTION

This invention provides an electrosurgical instrument having a conductive elongated member, a connector for connecting an external electrical power supply to the elongated member, an electrosurgical implement at the distal end of the elongated member, and an insulative parylene coating covering the elongated member. The thickness of the parylene coating is in the range of approximately 1 to 6 mil inches, and preferably 2 to 3.5 mil inches. In the preferred embodiment, the surfaces of the instrument that are to remain uncoated are first masked. The unmasked surfaces are roughened and then dipped in a liquid silicone. The parylene coating is then applied by vacuum vapor phase deposition and annealed. A parylene coating can also be applied to portions of the electrosurgical implement for insulation. A thin parylene coating can be applied to the blade of the instrument as a non-stick coating for easier cleaning. If the instrument is an endoscopic electrosurgical instrument used with a trocar sleeve having a valve to receive the shaft, wear between the valve and the shaft can be reduced by applying a parylene coating to the interior surface of the valve.

A primary object of the present invention is to provide an insulative coating having excellent dielectric properties for electrosurgical instruments.

Another object of the present invention is to provide an insulative coating for electrosurgical instruments that has good wear and adherence properties and that can withstand high temperatures associated with steam autoclave sterilization devices.

Yet another object of the present invention is to provide an insulative coating that can be readily applied to edges, ends, inner diameters, and corners of medical instruments.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which:

FIG. 1 is a side view of a typical electrosurgical instrument. A parylene coating has been applied to the shaft and selected portions of the implement located at the distal end of the electrosurgical instrument.

FIG. 2 is a cross-sectional view of the shaft of the electrosurgical instrument from FIG. 1 showing the parylene coating on its shaft.

DETAILED DESCRIPTION OF THE INVENTION

Figure 3:
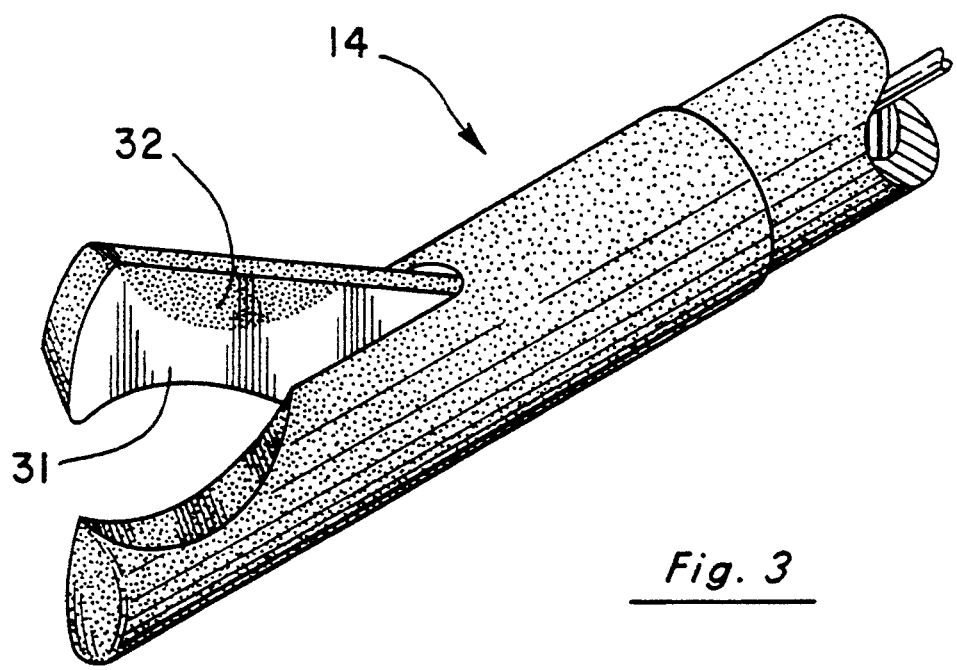
FIG. 3 is an enlarged perspective view corresponding to FIG. 1 showing the implement at the distal end of the electrosurgical instrument and the portions of the implement that have been coated with parylene.

Turning to FIG. 1, a side view is provided of a typical electrosurgical instrument 10 having a conductive elongated member (e.g., a metallic shaft) 12, an implement 14 at its distal end, and an electrical connector 16 for connecting an external electrical power supply to the proximal end of the shaft 12. An insulated grip 18 is provided at the proximal end of shaft 12 to allow manipulation of the instrument 10 by the surgeon. It should be understood that the instrument 10 shown in FIG. 1 is merely one example of the wide variety of electrosurgical instruments that can be coated using the present invention.

Figure 4:
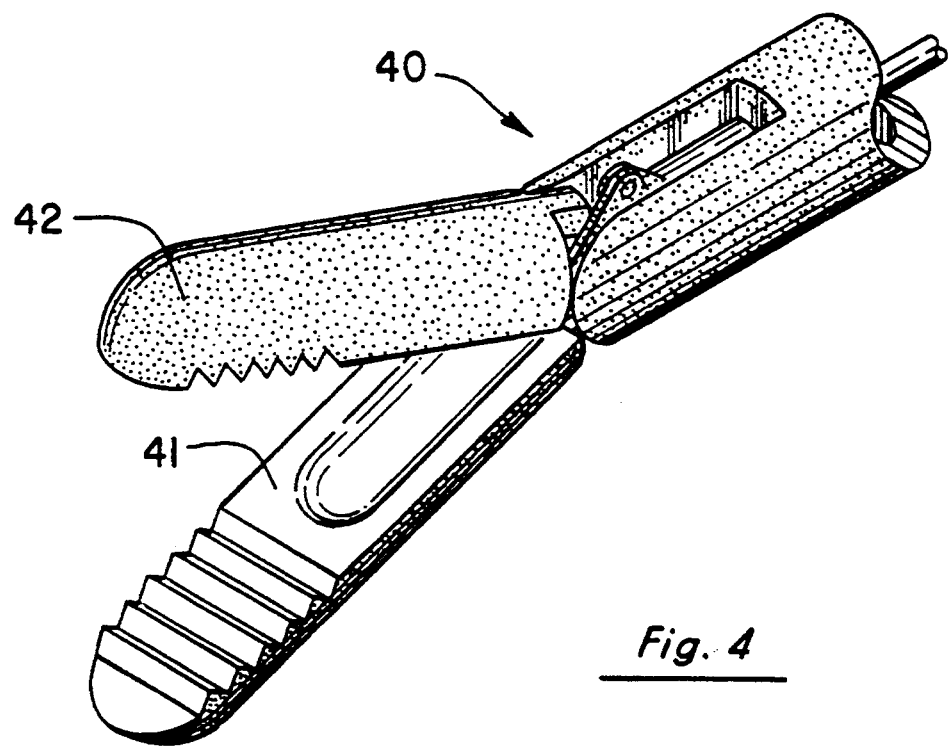
FIG. 4 is a perspective view of an alternative implement.
Figure 5:
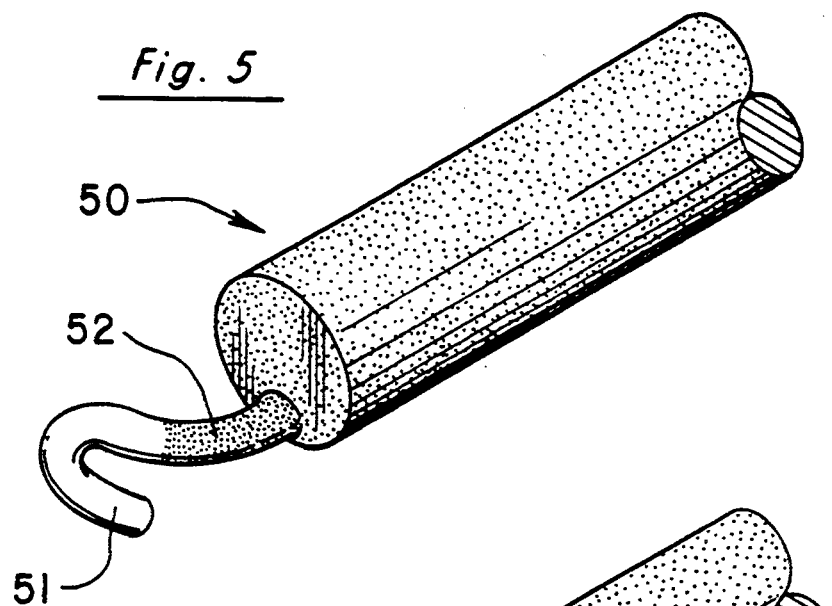
FIG. 5 is a perspective view of another alternative implement.
Figure 6:
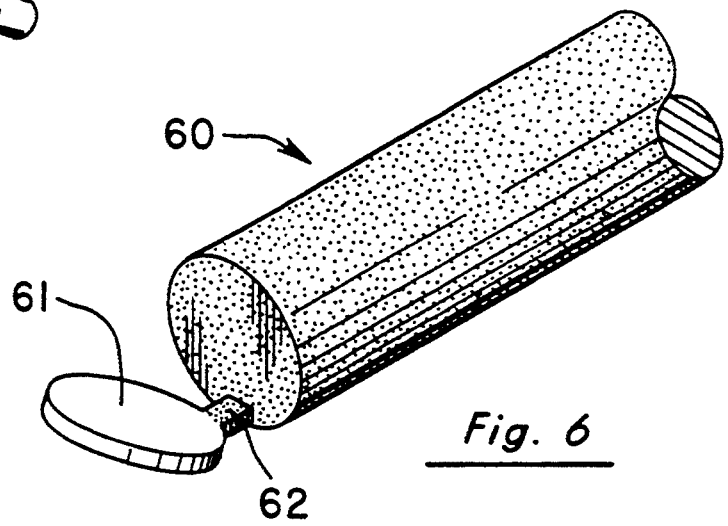
FIG. 6 is a perspective view of yet another alternative implement.

FIG. 2 is a cross-sectional view showing the parylene coating 20 applied to the shaft 12 of the instrument 10 of FIG. 1. FIG. 3 is a perspective view showing additional detail of the implement 14 at the distal end of the electrosurgical instrument 10 depicted in FIG. 1. In particular, selected portions of the surface of the implement 14 can also be covered with a parylene coating 32 while other portions 31 remain uncoated. Typically, the surfaces of the implement that are actually involved in cutting tissue remain uncoated. FIG. 4 is a perspective view of an alternative implement 40 that can be use for gripping tissue. Again, selected portions 42 of the implement are coated with parylene, while other portions 41 remain uncoated. FIGS. 5 and 6 provide additional examples of an implement 50 with a hook-shaped end and an implement 60 with a rounded end to demonstrate how a parylene coating can be selectively applied to desired portions 52, 62 of the implement, while other portions 51, 61 remain uncoated. Portions of the grip 18 can also be coated with parylene, if desired.

The instrument 10 is first masked to ensure that any desired metal surfaces that need to retain electrical conductivity are protected from being coated. This is generally accomplished with "platers" tape or preformed jigs or fixtures to mask selected portions of the instrument.

Next, the metal surfaces of the electrosurgical instrument are toughened to increase their surface area and thereby increase adherence of the monomer to the surfaces of the instrument. This can be accomplished by grit blasting using 60–70 mesh aluminum oxide. Typical tensile strengths of 10,000 have been measured with parylene coatings on metal substrates after utilizing this preprocessing technique. Alternatively, acid etchants can be used to increase the surface area of the instrument substrate.

The instrument is then dipped in an organic silicone, such as silane, to create a thin film on the surface of the instrument. Silane is a chemical coupling agent that allows the parylene the proper polar bonding characteristics to adhere to the instrument surface.

The instrument is then placed in a vacuum deposition chamber. A vacuum is drawn in the chamber to approximately 0.1 torr. A parylene dimer is added at approximately 150° C. A pyrolysis of the monomer is then affected at approximately 680° C. and 0.5 torr. The monomer enters the deposition chamber at approximately room temperature (approximately 25° C.) and simultaneously is adsorbed and polymerizes onto the substrate of the pre-masked instrument. The resultant coating is conformal, covering all exposed surfaces equally. Parylene C has been found to be the particular monomer of choice due to the economics of the rate of coating deposition. However, parylene types N, D, and E could be used separately, or in combination with each other, or with parylene C to form a hybrid coating.

The thickness of the resultant coating for electrosurgical instrumentation is in the range of approximately 1 to 6 mil inches, and preferably in the range of approximately 2 to 3.5 mil inches. This range accommodates all of the various ranges of electrosurgical generator voltages, frequencies, and current outputs presently in common use in the industry. In addition, this range accommodates those specific instrument applications where increased wear is a concern. For example, in endoscopic instruments, increased wear is inherent as the coated shaft of the instrument slides inside the trocar sleeve.

Finally, the coated instrument is annealed to increase its wear resistance and resistance to cutting. This is accomplished preferably by heating the coated instrument to approximately 160° C. in a vacuum of approximately 0.1 to 100 millitorr. Wear tests have been performed that indicate annealed parylene has wear resistance values that approximately equal to those of Teflon and high-impact polyvinyl chloride (PVC), which is more than sufficient in the medical or surgical fields of use. The annealed parylene coating offers the following advantages:

A. Bio-compatibility to level 6 (the highest level, suitable for implantation).
B. Excellent moisture vapor barrier properties (less than 0.25 via ASTM method "E" 96-63T), approximately 8 to 16 times less than other materials discussed above.
C. Operating temperatures to 150° C.
D. No degradation due to gamma ray sterilization techniques.
E. Virtually invariable dielectric constant (approximately 2.9 from 60 Hz–1 MHz).
F. Dielectric strength greater than 5000 volts/mil inch.
G. A low dissipation factor (approximately 0.0015) from 60 Hz–1 MHz.
H. A direct bond to the instrument that eliminates sterility problems associated with separation of the coating from the instrument.

This parylene coating has been found useful in all electrosurgical instrumentation applications, including monopolar, bipolar, endoscopic, laproscopic, and protective instrument applications (such as coating vaginal speculums to prevent accidental electrosurgical burns).

Figure 7:
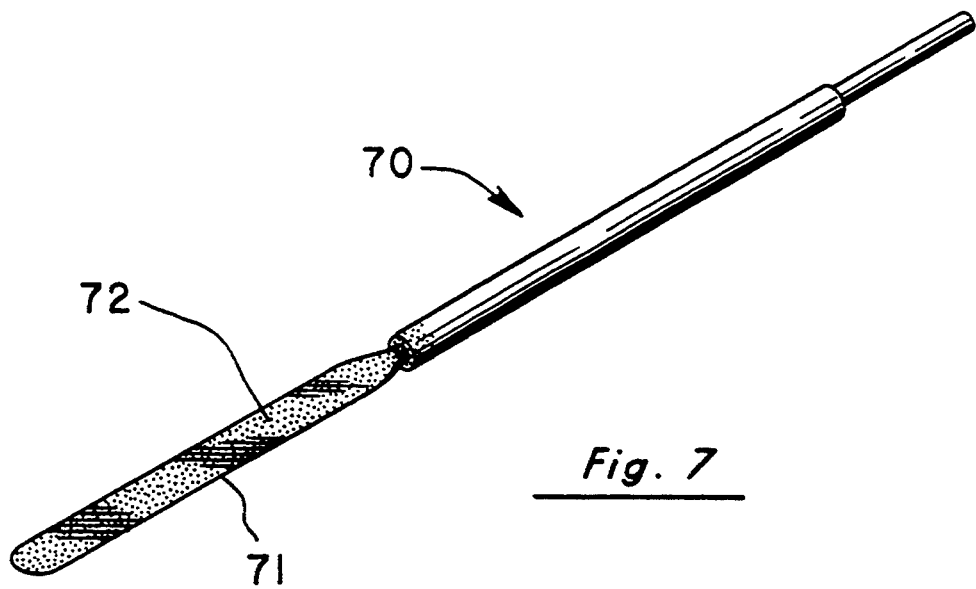
FIG. 7 is a perspective view of an electrosurgical blade with a parylene coating.

FIG. 7 is an example of a conventional electrosurgical blade 70 with a parylene coating 72 that covers the entire surface of the blade, including its cutting edge 71. In this embodiment, the shaft and main body of the blade are coated with parylene to a thickness of approximately 1 to 6 mil inches, as previously discussed. A much thinner parylene coating can be applied along the cutting edge 71 to provide a non-stick surface that minimizes adhesion of tissue to the blade. For example, a coating thickness in the range of approximately 0.01 to 0.2 mil inches along the cutting edge 71 has been found to be satisfactory for this purpose. The blade can be become extremely hot due the current densities involved. The thin non-stick coating provides thermal insulation between the tissue and blade that reduces burns and other thermal injury to the tissue. In addition, the thin non-stick coating provides a degree of electrical insulation to neighboring tissue without interfering with the effectiveness of the electrosurgical instrument in cutting tissue in immediate contact with the cutting edge of the blade. The thin parylene coating facilitates capacitive coupling between the blade and the tissue in immediate contact with the cutting edge of the blade and thereby allows transmission of sufficient radio-frequency electrical energy to cause hemostasis during surgery. In addition, the non-stick coating tends to gradually wear off during the course of surgery in the region immediately along the cutting edge of the blade. This tends to create small areas along the cutting edge in which the blade is exposed and can deliver relatively high current to the immediately adjacent tissue. However, the rest of the blade surface remains insulated by the non-stick coating.

Figure 8:
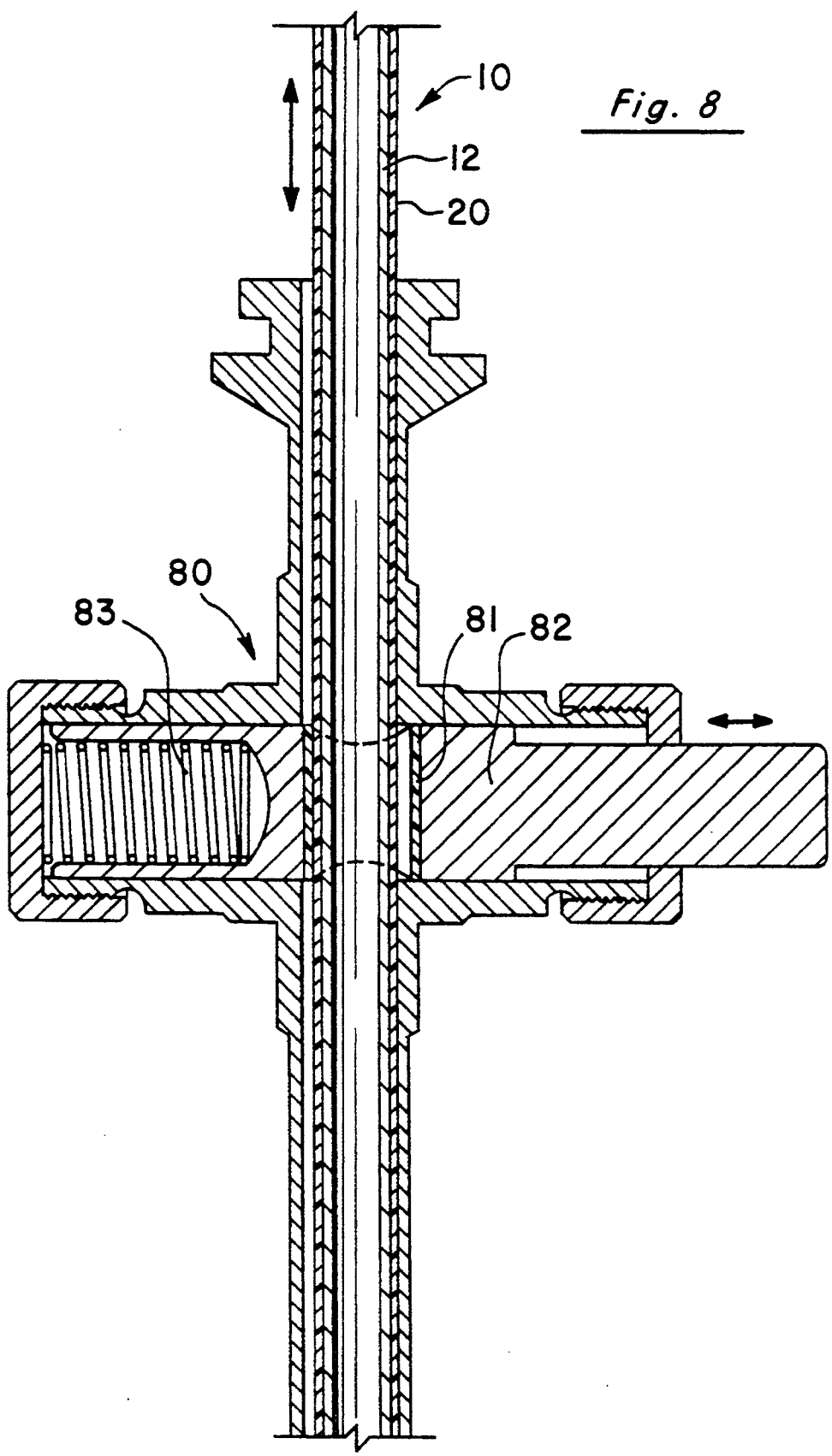
FIG. 8 is a fragmentary side cross-sectional view of a portion of the shaft of an endoscopic electrosurgical instrument inserted through a trocar sleeve having a spring-loaded valve to receive the shaft of the endoscopic electrosurgical instrument.

FIG. 8 shows a fragmentary side cross-sectional view of a portion of the shaft 12 of an endoscopic electrosurgical instrument 10 inserted through a trocar sleeve 80. The trocar sleeve 80 includes a valve assembly 82 that is spring-loaded 83 to receive the shaft 12 of the endoscopic electrosurgical instrument 10. A parylene coating 81 has been applied to the interior surface of the valve 82 to reduce wear between the valve 82 and the parylene coating 20 on the shaft 12 of the instrument 10.

Figure 9:
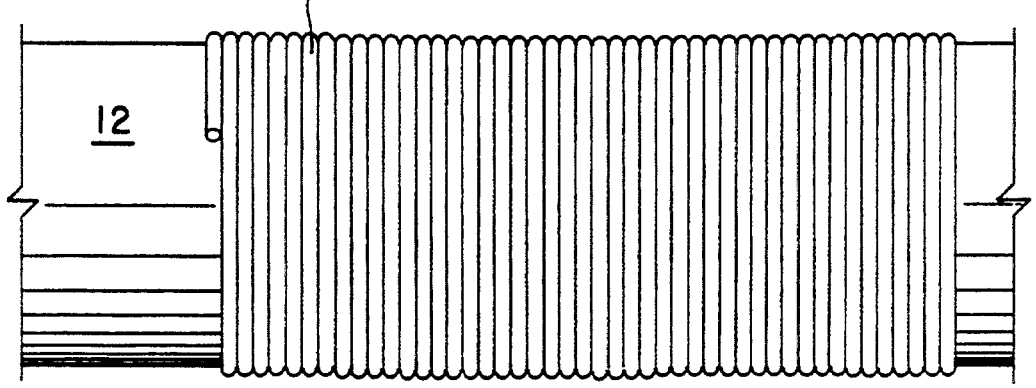
FIG. 9 is a fragmentary side view of the shaft of an electrosurgical instrument with a reinforcing fiber helically wrapped about a portion of the shaft.
Figure 10:
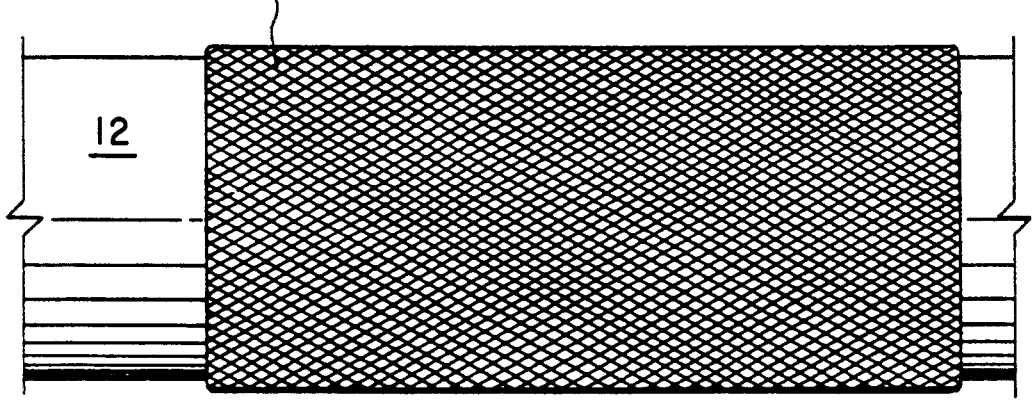
FIG. 10 is a fragmentary side view of the shaft of an electrosurgical instrument partially covered by a sleeve made of fabric.
Figure 11:
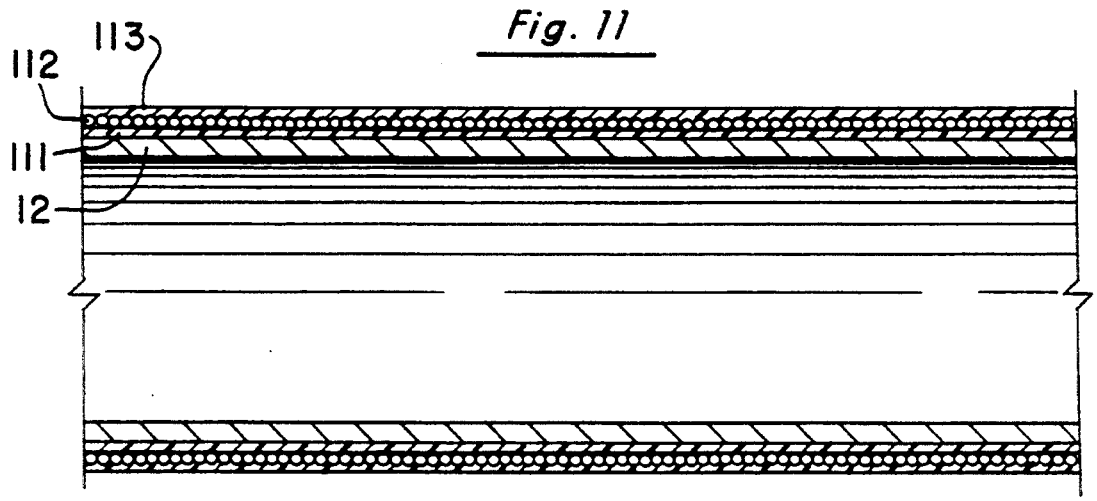
FIG. 11 is a fragmentary side cross-sectional view of the shaft of an electrosurgical instrument having a first parylene coating, an intermediate layer of fiber, and a second outer parylene coating.

FIGS. 9–11 show two alternative embodiments of the present invention in which high-strength fibers or fabric are used to reinforce the parylene coating. For example, fibers or fabric made of aramid (e.g., Nomex or Kevlar), a fluorinated hydrocarbon poller (e.g., Gore-Tex or Teflon), or nylon can be employed for this purpose. Gore-Tex is particularly suitable for this purpose because it is completely bio-compatible and is available in the form of a seamless woven tube that can be readily fitted over the shaft 12 of electrosurgical instruments. FIG. 9 is a fragmentary side view of the shaft 12 of an electrosurgical instrument with a reinforcing fiber 90 helically wrapped about a portion of the shaft 12 of the instrument. FIG. 10 is a fragmentary side view of the shaft 12 of an electrosurgical instrument partially covered by a sleeve 100 made of woven fabric. FIG. 11 is a corresponding side cross-sectional view of the shaft 12 of the electrosurgical instrument. An inner parylene coating 111 is first applied to the shaft 12, as previously described. A layer of fiber 112 (or fabric) is then wrapped over the first parylene coating 111. A second, outer parylene coating 113 is deposited on top of the fiber layer. The entire assembly is then annealed as previously described. The reinforcing fibers helps in resisting nicks, cuts, and abrasion and therefore substantially increases the useful life of the parylene coating.

The above disclosure sets forth a number of embodiments of the present invention. Other arrangements or embodiments, not precisely set forth, could be practiced under the teachings of the present invention and as set forth in the following claims.

I claim:

1. An electrosurgical instrument for use with a high-frequency electrical power supply during surgery on tissue, said instrument comprising:

a conductive elongated member having a proximal end and a distal end;

means for connecting said electrical power supply to said elongated member;

an electrosurgical implement at said distal end of said elongated member having at least one tissue-contacting surface formed thereon; and a parylene coating covering at least substantially all of said tissue-contacting surface of said electrosurgical implement having a thickness in the range of approximately 0.01 to 0.2 mil inches, thereby enabling said high-frequency electrical energy to be transported across said parylene coating by capacitive coupling; and a parylene coating covering at least a portion of said conductive elongated member.

2. The electrosurgical instrument of claim 1, wherein said parylene coating is annealed.

3. The electrosurgical instrument of claim 1, wherein said parylene coating is applied by vacuum deposition.

4. The electrosurgical instrument of claim 1, wherein said parylene coating covering said elongated member has a thickness of approximately 2 to 3.5 mil inches.

5. The electrosurgical instrument of claim 1, wherein said parylene coating covering said elongated member has a thickness of approximately 1 to 6 mil inches.

6. The electrosurgical instrument of claim 1, wherein said instrument is an endoscopic electrosurgical instrument further comprising a trocar sleeve having a valve to receive said elongated member, and wherein the interior surface of said valve has a parylene coating.

7. The electrosurgical instrument of claim 1, further comprising a grip extending from said proximal end of said elongated member, and wherein at least a portion of said grip has a parylene coating.

8. The electrosurgical instrument of claim 1, wherein said implement comprises a blade having a parylene coating.

9. The electrosurgical instrument of claim 1, wherein said implement comprises a hook having a parylene coating.

10. The electrosurgical instrument of claim 1, further comprising at least one reinforcing fiber in said parylene coating covering said elongated member.

11. The electrosurgical instrument of claim 10, wherein said reinforcing fiber is comprised of aramid.

12. The electrosurgical instrument of claim 10, wherein said reinforcing fiber is comprised of Gore-Tex.

13. The electrosurgical instrument of claim 10, wherein said reinforcing fiber is comprised of nylon.

14. The electrosurgical instrument of claim 1, wherein at least a portion of said conductive elongated member is covered with at least one reinforcing fiber and said parylene coating is applied over said reinforcing fiber.

15. An electrosurgical instrument for use with a high-frequency electrical power supply during surgery on tissue, said instrument comprising:

a conductive shaft having a proximal end and a distal end;

a grip at said proximal end of said shaft for manual manipulation of said instrument;

means for connecting said electrical power supply to said proximal end of said shaft;

an electrosurgical implement at said distal end of said shaft having at least one tissue-contacting surface formed thereon; and a parylene coating covering at least substantially all of said tissue-contacting surface of said electrosurgical implement having a thickness in the range of approximately 0.01 to 0.2 mil inches, thereby enabling said high-frequency electrical energy to be transported across said parylene coating by capacitive coupling; and a parylene coating covering at least a portion of said shaft.

16. The electrosurgical instrument of claim 15, wherein at least a portion of said grip has a parylene coating.

17. The electrosurgical instrument of claim 15, wherein said instrument is an endoscopic electrosurgical instrument further comprising a trocar sleeve having a valve to receive said shaft and wherein the interior surface of said valve has a parylene coating.

18. The electrosurgical instrument of claim 15, further comprising at least one reinforcing fiber in said parylene coating covering said shaft.

19. The electrosurgical instrument of claim 15, wherein at least a portion of said shaft is covered with at least one reinforcing fiber and said parylene coating is applied over said fiber.

20. An electrosurgical instrument for use with a source of high-frequency electrical energy during surgery on tissue, said instrument comprising:

an electrosurgical implement for receiving said high-frequency energy and having at least one tissue-contacting surface formed thereon; and a parylene coating covering at least substantially all of said tissue-contacting surface of said electrosurgical implement having a thickness in the range of approximately 0.01 to 0.2 mil inches, thereby enabling said high-frequency electrical energy to be transported across said parylene coating by capacitive coupling.

21. The electrosurgical instrument of claim 20, wherein said parylene coating is annealed.

22. The electrosurgical instrument of claim 20, wherein said parylene coating is applied by vacuum deposition.

23. The electrosurgical instrument of claim 20, wherein said implement comprises a blade.

24. The electrosurgical instrument of claim 20, wherein said implement comprises a hook.

25. The electrosurgical instrument of claim 20, wherein said implement comprises a spatula.

26. The electrosurgical instrument of claim 20 wherein said implement comprises a rounded surface.

27. The electrosurgical instrument of claim 20 wherein said implement comprises a needle.

* * * * *